(12) United States Patent
Imshenetskiy et al.

(10) Patent No.: US 11,427,770 B2
(45) Date of Patent: Aug. 30, 2022

(54) METHOD FOR PRODUCING HIGH-OCTANE MOTOR GASOLINES OF LOW-OCTANE HYDROCARBON FRACTIONS, FRACTIONS OF GASEOUS OLEFINS AND OXYGENATES AND A PLANT FOR THE METHOD EMBODIMENT

(71) Applicant: NGT Global AG, Zug (CH)

(72) Inventors: Vladimir Vladislavovich Imshenetskiy, Moscow (RU); Iosif Izrailevich Lischiner, Moscow (RU); Olga Vasilyevna Malova, Moscow (RU); Andrey Leonidovich Tarasov, Moscow (RU)

(73) Assignee: NGT Global AG, Zug (CH)

( * ) Notice: Subject to any disclaimer, the term of this patent is extended or adjusted under 35 U.S.C. 154(b) by 119 days.

(21) Appl. No.: 16/081,946

(22) PCT Filed: Mar. 7, 2017

(86) PCT No.: PCT/RU2017/050009
§ 371 (c)(1),
(2) Date: Sep. 3, 2018

(87) PCT Pub. No.: WO2017/155431
PCT Pub. Date: Sep. 14, 2017

(65) Prior Publication Data
US 2020/0291304 A1 Sep. 17, 2020

(30) Foreign Application Priority Data

Mar. 9, 2016 (WO) ............... PCT/RU2016/000127

(51) Int. Cl.
*C10G 35/095* (2006.01)
*B01J 29/40* (2006.01)
*C10G 3/00* (2006.01)

(52) U.S. Cl.
CPC .......... *C10G 35/095* (2013.01); *B01J 29/405* (2013.01); *C10G 3/49* (2013.01); *C10G 3/60* (2013.01);
(Continued)

(58) Field of Classification Search
CPC .......... C10G 3/49; C10G 3/60; C10G 35/095; C10G 2300/1037; C10G 2300/1088;
(Continued)

(56) References Cited

U.S. PATENT DOCUMENTS 3,702,886 A 11/1972 Argauer
3,756,942 A 9/1973 Cattanach
(Continued)

FOREIGN PATENT DOCUMENTS

RU 2160161 12/2000
RU 2284343 9/2006
(Continued)

OTHER PUBLICATIONS

U.S. Appl. No. 16/081,946, NGT Global AG.
(Continued)

*Primary Examiner* — Brian A McCaig
(74) *Attorney, Agent, or Firm* — Glen P. Belvis; Belvis Law, LLC.

(57) ABSTRACT

The invention relates to method and plant for the production of high-octane gasolines from raw hydrocarbon fractions, fractions of gaseous olefins and oxygenates. A method has been proposed, wherein the feedstock component flow is supplied to a unit for supplying flows to be treated, into the reactor, wherein the reaction is carried out in the presence of a zeolite-containing catalyst, high-octane gasoline is isolated by separation of the conversion product, while diverting simultaneously the reaction water and the exhaust gases. A reactor contains at least two reaction zones, between which
(Continued)

there are further arranged means for mixing the reaction product from the previous reaction zone and the supplied oxygenates and olefin-containing feedstock, whereas using the unit for supplying flows there is supplied a flow oxygenates and olefin-containing feedstock and the flow of raw hydrocarbon fractions into the first reaction zone of the reactor, and the flow oxygenates and olefin-containing feedstock into the second reaction zone of the reactor.

52 Claims, 2 Drawing Sheets

(52) U.S. Cl.
CPC ............. *C10G 2300/1037* (2013.01); *C10G 2300/1088* (2013.01); *C10G 2300/4006* (2013.01); *C10G 2300/708* (2013.01); *C10G 2400/02* (2013.01)

(58) Field of Classification Search
CPC ...... C10G 2300/4066; C10G 2300/708; C10G 2400/02; C07C 41/06; B01J 29/405; B01J 29/46; Y02P 30/20
See application file for complete search history.

(56) References Cited

U.S. PATENT DOCUMENTS

| | | | |
|---|---|---|---|
| 3,911,041 A | 10/1975 | Kaeding et al. | |
| 3,941,871 A | 3/1976 | Dwyer et al. | |
| 4,159,282 A | 6/1979 | Olson et al. | |
| 4,211,640 A | 7/1980 | Garwood et al. | |
| 4,227,992 A | 10/1980 | Garwood et al. | |
| 4,356,338 A | 10/1982 | Young | |
| 4,456,527 A | 6/1984 | Buss et al. | |
| 4,463,204 A | 7/1984 | Liu | |
| 4,465,886 A | 8/1984 | Rodewald | |
| 4,499,314 A | 2/1985 | Seddon et al. | |
| 4,523,049 A | 6/1985 | Jones et al. | |
| 4,554,260 A | 11/1985 | Pieters et al. | |
| 4,590,321 A | 5/1986 | Chu | |
| 4,720,602 A | 1/1988 | Chu | |
| 4,853,202 A | 8/1989 | Kuznicki | |
| 4,899,011 A | 2/1990 | Chu et al. | |
| 4,963,337 A | 10/1990 | Zones | |
| 5,108,579 A | 4/1992 | Casci | |
| 5,173,461 A | 12/1992 | Absil et al. | |
| 5,178,748 A | 1/1993 | Casci et al. | |
| 5,306,411 A | 4/1994 | Mazanec et al. | |
| 5,321,183 A | 6/1994 | Chang et al. | |
| 5,362,697 A | 11/1994 | Fung et al. | |
| 5,365,003 A | 11/1994 | Chang et al. | |
| 5,453,554 A | 9/1995 | Cheng et al. | |
| 5,498,814 A | 3/1996 | Chang et al. | |
| 5,516,736 A | 5/1996 | Chang et al. | |
| 5,536,894 A | 7/1996 | Degnan et al. | |
| 5,557,024 A | 9/1996 | Cheng et al. | |
| 5,935,897 A | 8/1999 | Trubenbach et al. | |
| 5,993,642 A | 11/1999 | Mohr et al. | |
| 6,046,372 A | 4/2000 | Brown et al. | |
| 6,063,724 A | 5/2000 | Resasco et al. | |
| 6,096,193 A | 8/2000 | Resasco et al. | |
| 6,143,166 A | 11/2000 | Nacamuli | |
| 6,413,898 B1 | 7/2002 | Faber et al. | |
| 6,423,879 B1 | 7/2002 | Brown et al. | |
| 6,504,072 B1 | 1/2003 | Brown et al. | |
| 6,635,792 B2 | 10/2003 | Choi et al. | |
| 6,906,232 B2 | 6/2005 | Levin et al. | |
| 6,995,111 B2 | 2/2006 | Levin et al. | |
| 7,026,263 B2 | 4/2006 | Le Van Mao | |
| 7,078,578 B2 | 7/2006 | Janssens et al. | |
| 7,122,492 B2 | 10/2006 | Ou et al. | |
| 7,122,493 B2 | 10/2006 | Ou et al. | |
| 7,164,052 B2 | 1/2007 | Carati et al. | |
| 7,208,442 B2 | 4/2007 | Xu et al. | |
| 7,419,930 B2 | 9/2008 | Carati et al. | |
| 7,700,816 B2 | 4/2010 | Xu et al. | |
| 7,923,399 B2 | 4/2011 | Long et al. | |
| 8,226,740 B2 | 7/2012 | Chaumonnot et al. | |
| 8,338,655 B2 | 12/2012 | Chang | |
| 9,040,003 B2 | 5/2015 | Andersen et al. | |
| 10,550,331 B2 * | 2/2020 | Lischiner | C10G 3/52 |
| 2008/0027255 A1 | 1/2008 | Blessing et al. | |
| 2008/0300434 A1 | 12/2008 | Cortright | |
| 2008/0300435 A1 | 12/2008 | Cortright | |
| 2009/0288990 A1 | 11/2009 | Xie et al. | |
| 2010/0145127 A1 | 6/2010 | Xie et al. | |
| 2013/0066126 A1 | 3/2013 | Jana | |
| 2013/0317269 A1 | 11/2013 | Nesterenko et al. | |
| 2014/0018592 A1 | 1/2014 | Chen et al. | |
| 2014/0058180 A1 | 2/2014 | Klingelhofer et al. | |
| 2014/0100404 A1 | 4/2014 | Narula et al. | |
| 2014/0256010 A1 | 9/2014 | Narula et al. | |
| 2014/0273146 A1 | 9/2014 | Narula et al. | |
| 2014/0322781 A1 | 10/2014 | Narula et al. | |
| 2017/0001922 A1 | 1/2017 | Lishchiner et al. | |
| 2017/0007992 A1 | 1/2017 | Lishchiner et al. | |
| 2017/0145317 A1 | 5/2017 | Lischiner et al. | |
| 2017/0233311 A1 | 8/2017 | Vladislavovich et al. | |

FOREIGN PATENT DOCUMENTS

| | | |
|---|---|---|
| RU | 2289477 | 12/2006 |
| RU | 2293056 | 2/2007 |
| RU | 2294799 | 3/2007 |
| RU | 2320631 | 3/2008 |
| RU | 2323777 | 5/2008 |
| RU | 2333033 | 9/2008 |
| RU | 2349567 | 3/2009 |
| RU | 2349568 | 3/2009 |
| RU | 2350591 | 3/2009 |
| RU | 2350592 | 3/2009 |
| RU | 2354638 | 5/2009 |
| RU | 2354639 | 5/2009 |
| RU | 2362760 | 7/2009 |
| RU | 2391135 | 6/2010 |
| RU | 2009101606 | 7/2010 |
| RU | 2429910 | 9/2011 |
| RU | 2433863 | 11/2011 |
| RU | 2440189 | 1/2012 |
| RU | 2446135 | 3/2012 |
| RU | 2010135608 | 3/2012 |
| RU | 2454388 | 6/2012 |
| RU | 2458898 | 8/2012 |
| RU | 2466976 | 11/2012 |
| RU | 2477656 | 3/2013 |
| RU | 2495017 | 10/2013 |
| RU | 2509759 | 3/2014 |
| RU | 2518091 | 6/2014 |
| RU | 2544017 | 3/2015 |
| RU | 2544241 | 3/2015 |
| RU | 2549571 | 4/2015 |
| RU | 2550354 | 5/2015 |
| RU | 2558955 | 8/2015 |
| WO | WO 1996/016004 | 5/1996 |
| WO | WO 2008/109877 | 9/2008 |
| WO | WO 2015/115932 | 8/2015 |
| WO | WO 2015/112056 | 9/2015 |
| WO | WO 2015/147700 | 10/2015 |
| WO | WO 2016/024883 | 2/2016 |
| WO | WO 2017/155424 | 9/2017 |

OTHER PUBLICATIONS

U.S. Appl. No. 16/081,947, NGT-S.
U.S. Appl. No. 16/195,022, NGT Global AG.
May 1, 2004, Yuan, Alkylation of benzene with ethanol ver ZSM-5 Catalyst (Indian Journal of Chemical Technology, vol. 1, May 2004, pp. 337-345).
Aug. 29, 2017, EPO, EP 14 881 043.5 Report.
May 15, 2018, EPO, EP 15 741 108.3 Report.
May 26, 2017, EPO, EP 15 741 108.3 Extended Report.

(56) References Cited

OTHER PUBLICATIONS

Oct. 26, 2017, EPO, EP 15 768 758.3 Report.
Feb. 12, 2018, EPO, EP 15 831 280.1 Report.
Feb. 13, 2017, RU patent Office, 201600533 Office Action.
RU patent Office, 201600532 Office Action.
RU patent Office, 201600667 Office Action.
Apr. 28, 2018, RU patent Office, 201700105 Office Action.

* cited by examiner

METHOD FOR PRODUCING HIGH-OCTANE MOTOR GASOLINES OF LOW-OCTANE HYDROCARBON FRACTIONS, FRACTIONS OF GASEOUS OLEFINS AND OXYGENATES AND A PLANT FOR THE METHOD EMBODIMENT

This application is a US nationalization pursuant to 35 U.S.C. § 371 of PCT/RU2017/050009 filed Mar. 7, 2017, which claims priority to PCT/RU2016/000127 filed Mar. 9, 2016; and, is a US nationalization pursuant to 35 U.S.C. § 371 of PCT/RU2016/000127 filed Mar. 9, 2016, the entire disclosure of each of which is incorporated herein by reference.

FIELD OF THE INVENTION

The invention relates to petrochemistry, and more specifically, to methods and plants for the production of a base for the production of high-octane gasolines or high-octane gasoline components (concentrates of alkylaromatics) from raw hydrocarbon fractions, fractions of gaseous olefins and oxygenates, wherein starting components are mixed, feedstock is heated and supplied into a reactor, in which the reaction is carried out in the presence of a zeolite-containing catalyst, a gasoline base with improved antiknock rating or a concentrate alkylaromatics is isolated by the separation of the conversion product, while diverting simultaneously the reaction water and exhaust gases.

This description uses the following terms.

Gasoline is the main component of gasolines with improved antiknock rating for the production of commercial automotive and aviation gasolines with a low content of benzene, sulfur compounds and olefins, durene, and with no diene hydrocarbons in the composition, or a concentrate of alkylaromatics.

Concentrate of alkylaromatics (interchangeable with concentrate alkylaromatics) is aromatic hydrocarbon concentrate with the total content of alkyl-substituted aromatics (e.g. xylenes, ethylbenzene) exceeding the total content of non-alkyl-substituted aromatics (e.g. benzene, naphthalene).

Feedstock hydrocarbon fractions (interchangeable with raw hydrocarbon fractions) are various hydrocarbon fractions, such as 1) straight-run fractions; 2) fractions of hydrocarbons with higher benzene content, including, for example, a benzene fraction made of straight-run gasoline reformates; 3) fractions containing components prone to resin formation, such as dienes and aromatic olefins, including light fractions of pyrolysis gasolines and mixtures thereof with other fractions; 4) hydrocracking gasolines; 5) stable natural gasoline; 6) gas condensate distillate; and other similar products and mixtures thereof.

Methanol and/or other oxygenates and/or olefin-containing feed-stock, which means that a mixture of methanol and/or other oxygenates, including ethanol and water, and, in addition to or instead of it, a light olefin-containing feed-stock, such as various ethylene fractions, propane-propylene fractions, butane-butylene fractions, broad olefin containing fractions and mixtures thereof can be used. Thus, the feedstock can include in addition to the raw hydrocarbon fractions one or more of the following: methanol, ethanol, oxygenates, water, light olefins, light-olefinic fractions and combination and variations of these.

Methanol and/or other oxygenates are various oxygenate fractions that can include one or more of the following: methanol, crude methanol, a mixture of alcohols, mixture of their ethers, water and combination and variations of these.

Zeolite-containing catalyst is one or a mixture of zeolite-containing catalysts used in processes of hydrocarbon and/or oxygenates and/or olefin conversion, such as 1) co-processing of oxygenates with hydrocarbons into predominantly gasoline-range hydrocarbons; 2) conversion of methanol into hydrocarbons; 4) co-processing of olefins with hydrocarbons; 5) olefin to gasoline processes; 6) catalytic deparaffinization; and other similar processes and combinations thereof.

Reaction water is the water chemically created during the production of gasoline from oxygenate-containing feedstock.

RON stands for the Research Octane Number. It is determined by the method described in GOST 8226-82: "The method is to compare the antiknock rating of test fuel with the antiknock rating of reference fuels expressed by the octane number" on a bench motor. RON characterizes the behavior of a gasoline engine in the modes of small and medium loads. To assess RON, there are also used indirect methods based, for example, on the analysis of chromatograms of gasoline or the analysis of the characteristics of the low-temperature gas-phase oxidation reaction simulating pre-ignition processes, or by the measurement of indirect gasoline physical quantities that correlate well with RON indicators, measured in accordance with GOST 8226-82. Measurement tools for indirect RON assessment are called Octane meters.

BRON stands for motor fuel component blending RON that is determined by calculation based on the analysis of RON of mixture of this component and straight-run gasoline taken in predetermined weight or volume ratios and analysis of straight-run gasoline RON (only weight BRONs are considered here). Analogous BRON can be calculated for other hydrocarbon fractions besides straight-run gasoline.

Reaction zone is an isolated space in a reactor, where the catalyst is located.

This description refers to the production of a major component of commercial gasoline. In some cases, depending on the feedstock, the conversion product may contain fractions having temperatures of over 210° C. in an amount of more than 2 vol %, which does not meet the commercial gasoline requirements published in the European Norm EN 228:2008.

Prior Art of the Method

One of the aspects of the present group of inventions relates to methods for producing motor gasolines having an improved antiknock rating of the raw hydrocarbon fractions, fractions of gaseous olefins and oxygenates, where the starting components are mixed, the feedstock is heated and supplied into a reactor, wherein the reaction is carried out in the presence of a zeolite-containing catalyst, high-octane gasoline is isolated by separation of the conversion product, while diverting simultaneously the reaction water and exhaust gases.

The U.S. Pat. No. 2,429,910 of the Russian Federation for the invention, which was published in 2011, described a method for co-processing of low-octane hydrocarbon fractions and aliphatic alcohols and/or dimethyl ether.

This method is the closest to the present invention and is taken as the prototype for the method.

As an example of use of a reactor, the patent referred to the Patent No. 65045 of the Russian Federation for utility model No. 65045, which was published in 2007, which describes a plant for the production of synthetic gasoline from aliphatic alcohol, in particular, methanol, where a reactor with coaxial heat pipes is proposed. The heat pipes, due to coolant evaporating and condensing processes occurring in them, allow efficient redistribution of heat from heating zones adjacent to the surface of the heat pipes to heated zones also adjacent to the surface of the heat pipes. The distance between the surfaces of the heat pipes limiting the reactor space in the reactor described in the prior art should be no more than 150 mm. The ratio of the reaction zone volume to the reactor volume will be less than 0.3-0.5. Using another configuration of the heat pipes, for example as described in the U.S. Pat. No. 2,433,863 of the Russian Federation, which was published in 2011, does not solve this problem either, because the reactor (reaction zone) volume increases as the square of its diameter and the required surface of the heat pipes necessary for the heat exchange with the reaction zone depends linearly on the volume of the reaction zone. Thus, the use of reactors with the heat pipes does not allow achieving any reduction in metal consumption of the reactor structure. This limits the creation of a large-scale reactor with heat pipes having a capacity of dozens and hundreds of cubic meters.

Furthermore, a part of the reactor space between the heat pipes, when it is used in the process described in the prototype, is used to heat the feedstock supplied into the reactor in order to provide the coolant condensation on the inner surface of the heat pipes in an amount necessary for removing heat from the inlet (front) catalyst bed, where exothermic reactions prevail, and where the heat removal is performed by evaporation of coolant in the inner space of the heat pipe. Thus, according to Examples 3-9 and 11-17 in the U.S. Pat. No. 2,433,863 of the Russian Federation, feedstock is supplied into the reactor at a temperature of up to 100-205° C.

Thus, another disadvantage of this method is the limitation of production capacity of motor gasolines due to limiting the possibility of increasing the efficient and overall reactor volumes.

The third disadvantage of this method is the inability to control the temperature throughout the catalyst bed. Thus, in the lower catalyst bed, where the endothermic reactions prevail, the temperature will always be lower than the coolant condensation temperature on the heat pipe walls. The temperature in the input (front) part of the catalyst bed, where the exothermic reactions prevail and where the heat removal is performed by evaporation of the coolant flowing over the surface of the heat pipes from above the condensation zone will always be higher than the temperature of coolant condensation/evaporation in the heat pipe. Thus the temperature at the top of the reaction zone will always be higher by 15-45° C. than the temperature at the bottom of the reactor. This leads to the fact that it is impossible to adjust the temperature at the bottom of the catalyst bed, without increasing the temperature at the top (front) part of the catalyst bed in the reaction zone limited by the heat pipe space. Thus, if during operation, the conversion of methanol is reduced down to 99.5%, which will lead to an increase in the content of methanol in the reaction water, it is advisable to raise the temperature in the lower catalyst bed by 1-2° C.

Another disadvantage of this method is the fact that upon increasing the methanol to hydrocarbon ratio, the amount of heat generated in the front catalyst bed increases too. This, in turn, limits the temperature of feedstock being supplied to the reactor as the feedstock of a lower temperature is supplied to the reactor and is superheated exactly in the reactor in the area limited by the surface of the heat pipes located upstream the front bed, which is necessary for creating a sufficient coolant condensation on the surface of the heat pipes to dissipate heat.

Another drawback of the described method is restrictions by the fractional composition of feedstock. Thus, according to the method described in the prototype, the feedstock is supplied into the reactor in the gaseous phase at a temperature of no higher than 210° C., at the same time, the boiling point of n-octane will be 233° C. at 1 MPa, which is higher by 23° C. than indicated in the prototype.

Therefore, another drawback of this method is deterioration of the plant's capability of recycling feedstock having various fractional composition. Indeed, the normal boiling temperature of n-octane is 126° C., and its boiling point is 233° C. at the pressure of 1 MPa, which does not allow using octane as feedstock at a pressure in the reaction zone of higher than 1 MPa.

Yet another drawback of the proposed method is that the high concentrations of light olefins and oxygenates in the feedstock, in particular, of methanol, dimethyl ether, ethylene lead to increased formation of heavy compounds contained in the conversion product liquid hydrocarbon fractions; some of these compounds have high melting points, the presence of which is undesirable in commercial gasolines and usually their concentration is no more than 2% by weight.

SUMMARY OF THE INVENTION AS A METHOD

The present invention mainly aims to propose a method of producing gasoline from raw hydrocarbon fractions, fractions of gaseous olefins and oxygenates, wherein the starting components flow is supplied to a unit for supplying the flow to be processed into a reactor, wherein the reaction is carried out in the presence of a zeolite-containing catalyst, gasoline is isolated by separation of the conversion product, while diverting simultaneously the reaction water and the exhaust gases, allowing improvement of the quality of the resulting gasoline by reducing the content of benzene in it, as well as refractory components, such as durene, as well as by the possibility of regulating the temperature throughout the catalyst bed without the use of complex heat exchange reactor equipment, as well as the possibility of increasing the useful volume of the reactor equipment, which is the technical problem specified.

To solve the specified technical problem, as a reactor, a reactor is used, which contains at least two reaction zones with a zeolite-containing catalyst, between which there are further arranged means for mixing the reaction product from the previous reaction zone and the supplied methanol and/or other oxygenates and/or olefin-containing feedstock, whereas using the unit for supplying flows there is supplied the separated and/or pre-mixed flow of methanol and/or other oxygenates and/or olefin-containing feedstock and the flow of raw hydrocarbon fractions into the first reaction zone of the reactor, and the flow of methanol and/or other oxygenates and/or olefin-containing feedstock into the second or subsequent reaction zone of the reactor.

An example of such a reactor can be a vertical multiple-shell reactor or a horizontal reactor, the housing of which accommodates several series-connected catalyst baskets; an example of such solutions using a horizontal reactor is shown in FIG. 2. An example of such a reactor can be single or multibed reactor or reactor system, such as arrangement of reactors in series, arrangement of reactors in parallel and combinations thereof. An example of such a reactor can be fixed bed reactor, fluidized bed reactor, reactors designed for continuous catalyst regeneration. An example of such a reactor can be isothermal, adiabatic or pseudo-isothermal reactor.

An example of the catalyst can be catalysts described hereinafter.

Due to these favorable characteristics, the following possibility appears:
- Increase in RON of gasolines produced using the method described;
- Reduction of the content of undesired compounds therein with high melting points and being prone to crystallization, such as, for example, durene, 2,6-dimethylnaphthalene;
- Reduction of the content of benzene therein, which is a toxic and carcinogenic substance having the maximum volatility (fugacity) among other aromatics;
- Increase in production of gasoline of higher quality and with an improved antiknock rating due to the possibility of increasing the reactor capacity.

In one of the embodiments, methanol and/or other oxygenates and/or olefin-containing feedstock are separated by means of said unit into at least two flows, the first flow is directed into the space upstream the first reaction zone where it is mixed with the flow of raw hydrocarbon fractions, and the next flows are mixed in the downstream reaction zones with the conversion product from the upstream reaction zone.

In another embodiment one or more of the reaction zones can be not supplied with flows of methanol and/or other oxygenates and/or olefin-containing feedstock as long as at least two reaction zones are supplied with the flows of methanol and/or other oxygenates and/or olefin-containing feedstock.

In another embodiment, methanol and/or other oxygenates and/or olefin-containing feedstock are separated by means of said unit into at least one flow, which is directed to the downstream reaction zone, where said stream is mixed with the conversion product from the upstream reaction zone, wherein the first reaction zone is pre-supplied with a pre-mixed flow of methanol and/or other oxygenates and/or olefin-containing feedstock and the flow of raw hydrocarbon fractions. The flow of methanol and/or other oxygenates and/or olefin-containing feedstock is mixed with the raw hydrocarbon fractions in the space upstream the first reaction zone or more upstream in the direction of the hydrocarbon feedstock supply flow, and prior to supplying to the first reaction zone, the mixed flow of methanol and/or other oxygenates and/or olefin-containing feedstock and the flow of raw hydrocarbon fractions are heated, e.g., they may be preheated prior to mixing, during mixing or upon mixing, or prior to or upon introduction into the reaction zone.

In another embodiment flows of raw hydrocarbon fractions and flows of methanol and/or other oxygenates and/or olefin-containing feedstock can be heated prior to mixing, during mixing or upon mixing, or prior to or upon introduction into the reaction zone.

In another embodiment one or more reaction zones can be supplied with at least part of the raw hydrocarbon fraction flow.

The flow is directed from the unit said in the above five embodiments into the reaction zone directly or through a mixing zone located between the reaction zones and having means for mixing.

Indeed, the distributed supply allows improving the quality of the produced base stock for the production of gasoline by increasing the concentration of components having a high BRON, such as meta- and para-xylenes, in the resulting product, and allows reducing the concentration of undesirable durene, methylnaphthalenes having high melting temperatures, significantly decreasing the concentration of normal C6+ paraffins having an extremely low antiknock ratings, as well as significantly reducing the benzene content (see comparative Table 3 for examples No. 2 and No. 3).

Furthermore, the use of a reactor with supply of methanol and/or other oxygenates and/or olefin-containing feedstock to each or at least two reaction zones allows increasing production due to the ability to increase the efficient and total reactor volume. Thus, there is the possibility to simultaneously control the parameters of resulting gasoline due to the possibility to control the supply of methanol and/or other oxygenates and/or olefin-containing feedstock to the first and/or downstream reaction zones and/or the temperature of the mixture supplied to the first reaction zone or downstream reaction zones If methanol and/or other oxygenates and/or olefin-containing feedstock is supplied for the conversion by not a single flow, but divided into 2-5 flows and added to the converted mixture successively prior to supplying the converted mixture into the downstream reaction zone, and there is a mixing device installed upstream each downstream reaction zone, the function of which can also be carried out by a protective bed (precontact) poured over the catalyst bed in a catalytic basket, and the function of the mixing device can also be performed by a channel connecting the catalyst baskets to be placed in a horizontal reactor, this will allow using a vertical or horizontal reactor of simple design, with a high efficiency of the reactor volume.

In one of the embodiments, function of a mixing device is carried out by a protective bed of neutral or weakly-reacting material, for example quartz, in forms such as granules; spheres; fraction of crushed materials.

In one of the embodiments, function of a mixing device is carried out by a channel connecting the reactor spaces where the reaction zones are located.

In one of the embodiments, function of a mixing device is carried out by specifically controlled speed and/or direction of supplied feedstock flow, e.g. by using tangential supply of methanol and/or other oxygenates and/or olefin-containing feedstock to the reaction zone.

In one of the embodiments, the flow rate of methanol and/or other oxygenates and/or olefin-containing feedstock to each reaction zone is controlled, and the temperature of the feedstock to be supplied to the reaction zone is controlled so that the maximum catalyst bed temperature in the reaction zone does not exceed 420° C. in the production of a base stock for the production of gasolines and 500° C. in the production of alkylaromatics concentrate.

Additionally, when decreasing the supply of methanol and/or other oxygenates and/or olefin-containing feedstock to the first reaction zone, the temperature of raw mixture supplied into the first reaction zone can be increased, and vice versa.

Additionally, when decreasing the supply of methanol and/or other oxygenates and/or olefin-containing feedstock to the reaction zone, the temperature of raw mixture supplied into the reaction zone can be increased, and vice versa.

Indeed, the optimal solution is the option of supplying methanol and/or other oxygenates and/or olefin-containing feedstock into the reaction zones so that the heating temperature of the catalyst bed in the reaction zone does not exceed 420° C. in the production of the base stock for the production of high-octane gasoline and 500° C. in the production of alkylaromatics concentrate, whereas the temperature of the catalyst end bed should be respectively by 40-70° C. below said maximum temperature. Meanwhile, this raw mixture can be supplied to the first reaction zone at a reduced temperature of up to 310° C., whereby most of the methanol and/or other oxygenates and/or olefin-containing feedstock can be supplied to the first reaction zone, which allows controlling the supply of methanol and/or oxygenates and/or olefin-containing feedstock to the process by increasing the temperature of the feed-stock mixture supplied into the first reaction zone while reducing the consumption of methanol and/or other oxygenates and/or olefins; and vice versa, decreasing the feedstock mixture temperature while increasing the flow rate of methanol and/or other oxygenates and/or olefins.

Additionally, if it is necessary to increase the flow rate of methanol and/or other oxygenates and/or olefins to the second and/or downstream shelves/reaction zones, methanol and/or other oxygenates and/or olefins may be supplied at a lower temperature to prevent overheating of the front bed resulting in rapid deactivation of the catalyst and higher gassing.

Additionally, if it is necessary to decrease the temperature of the second and/or downstream reaction zones, methanol and/or other oxygenates and/or olefins may be supplied at a lower temperature to prevent overheating of the front part of the zone resulting in rapid deactivation of the catalyst and higher gassing.

In one of the embodiments, the flow rate of methanol and/or other oxygenates and/or olefin-containing feedstock to each reaction zone is regulated independently.

Due to this advantageous characteristic, there appears a possibility to mitigate uneven catalyst deactivation among reaction zones.

Example 1 of this patent provides information regarding adiabatic heating of the front catalyst bed during the conversion of hexane-heptane fraction mixture (83.5 wt. %), methanol (6.6 wt. %), water (7 wt. %) and ethylene fraction (2.9 wt. %). Adiabatic heating of the front catalyst bed in an isothermal reactor was about 60-65° C., while, due to the conversion of n-hexane, n-heptane and naphthenes contained in the hydrocarbon phase, the catalyst temperature in the end catalyst zone was about 350-360° C.

There is an embodiment, wherein raw hydrocarbon fractions or a mixture of raw hydrocarbon fractions and methanol and/or other oxygenates and/or olefin-containing feedstock are heated in two stages: at the first stage, raw hydrocarbon fractions or a mixture of raw hydrocarbon fractions and methanol and/or other oxygenates and/or olefin-containing feedstock are vaporized, heavier non-evaporated components are separated, and at the second stage the vaporized components are heated, e.g., preferably superheated.

Due to this advantageous characteristic, there appears a possibility to reduce the content of heavy high-boiling components in gasoline and reduce the coking rate of the catalyst, reduce potential coke deposition on the inner surface of pipes and hydrocarbon heating unit.

There is, moreover, an embodiment, wherein raw hydrocarbon fractions and methanol and/or other oxygenates and/or olefin-containing feedstock are supplied to the first reaction zone with joint flow. Due to this advantageous characteristic, there appears a possibility not to use any mixing device in the first reaction zone; also, the presence of water in the raw mixture inhibits radical oligomerization of dienes and aromatic olefins while heating the raw mixture, whereby they may be present in the raw hydrocarbon fractions.

There is also an embodiment, wherein raw hydrocarbon fractions and methanol and/or other oxygenates and/or olefin-containing feedstock are supplied to each reaction zone by separate flows, wherein they are pre-mixed, and a bed of granules of neutral material and/or a fraction of the crushed quartz placed upstream the frontal catalyst bed is used as a mixing device, or a line connecting the reactor spaces, where the reaction zones are located, is used as a mixing device. Due to this advantageous characteristic, there appears a possibility to use the protective catalyst bed or the line connecting the reaction zones or the line through which the mixture is supplied into the first reaction zone, as a mixing bed.

There is also an embodiment, wherein methanol and/or other oxygenates and/or olefin-containing feedstock are supplied by separate flows to the first or second and each downstream reaction zones, where methanol and/or other oxygenates are supplied in the gaseous phase at a temperature of no more than 380° C., which prevents its decomposition upon heating. Due to this advantageous characteristic, there appears a possibility to reduce the loss of methanol for its conversion to carbon oxides during heating up to higher temperatures.

There is also an embodiment, wherein methanol and/or other oxygenates and/or olefin-containing feedstock are supplied by separate flows to the first and/or second and/or subsequent reaction zones, where methanol and/or other oxygenates are supplied in the gaseous phase at a temperature of no more than 380° C., which prevents its decomposition upon heating. Due to this advantageous characteristic, there appears a possibility to reduce the loss of methanol for its conversion to carbon oxides during heating up to higher temperatures and possibility of finite control of temperature and/or chemical composition of the product of each reaction zone by controlling the amount of methanol and/or other oxygenates and/or olefin-containing feedstock coming to each reaction zone.

There is an embodiment, wherein a 1-2% aqueous solution of an industrial demulsifier is added to a mixture of hydrocarbons and water supplied to the separation at a ratio of 1:50-1:200 to the volume of the reaction water, the aqueous solution of the demulsifier is mixed with the input flow in a laminar static mixer or directly in a hydrocarbons and reaction water condenser located in the separation unit. Due to this advantageous characteristic, there appears a possibility to separate efficiently the mixture of reaction water and liquid hydrocarbons (conversion product) in the separation unit, as well as to prevent entrainment of catalyst particles with the liquid products of conversion and catalyst dust deposition on the surface of internal devices of fractionation columns.

There is an embodiment, wherein isothermal reaction zones are used as the last one or two reaction zones of the reactor.

Due to this advantageous characteristic, there appears a possibility to use the proposed invention at a low flow rate of methanol and/or other oxygenates and/or olefin-containing feedstock per ton of convertible hydrocarbon feedstock. Indeed, at low flow rates of methanol less than 20% by weight of the converted feedstock weight, to enhance RON of convertible mixtures, the proposed combined embodiment can be used, wherein the heat input to the last or to the penultimate and last reaction zones can be performed directly to the reaction zone. Moreover, it allows increasing the temperature in the last reaction zone in order to increase the methanol and/or other oxygenates and/or olefin-containing feedstock conversion as it de-creases and with a decrease of catalyst activity during its use.

There is also an embodiment, wherein adiabatic reaction zones containing no heat exchange devices are used as the last one or two reaction zones of the reactor, at the same time, the feedstock flow to be supplied to the final and/or penultimate reaction zones is further heated, e.g., preferably superheated no more than up to 500° C.

Due to this advantageous characteristic, there appears a possibility to use the proposed invention at a low flow rate of methanol and/or other oxygenates and/or olefin-containing feedstock per ton of converted hydrocarbon feedstock. Indeed, at low flow rates of methanol less than 20% by weight of the weight of converted feed-stock, to enhance RON of convertible mixtures the proposed combined embodiment can be used, wherein the heat input to the last or the last and the penultimate reaction zones can be carried out by heating, preferably preheating, the converted feedstock to 500° C. before it is supplied to the respective reaction zones. This embodiment with the supply of heat to the last or the last and the penultimate reaction zones has also the advantage that with an increase in the useful volume of the reactor, the temperature can be adjusted in the last or the last and the penultimate reaction zones in the direction of the feedstock flow, regardless of the temperature in the first reaction zones (in the direction of the feedstock flow).

There is also an embodiment, wherein pseudo-isothermal reaction zones are used as the last one or two reaction zones of the reactor. In this embodiment, reaction zones contain heat-exchange devices which are unable to sustain constant temperature throughout all of the reaction zone but can partially mitigate temperature difference between front and end parts of the reaction zone without escalating the low of methanol and/or other oxygenates and/or olefin-containing feed-stock supplied to the reaction zone.

Due to this advantageous characteristic, there appears a possibility to use the proposed invention at a lower flow rate of methanol and/or other oxygenates and/or olefin-containing feedstock per ton of converted hydrocarbon feedstock.

There is another embodiment, wherein separated reaction water with an admixture of methanol and/or other oxygenates, is supplied to a distillation column, the distillation residue of which is water cleaned from residues of hydrocarbons with a reduced content of methanol and/or other oxygenates and the distillate of which is water with an increased content of oxygenates and hydrocarbons, while oxygenates, e.g. preferably methanol water and hydrocarbons produced during the distillation process are recycled to the reactor inlet to the beginning of the process in a mixture with methanol and/or other oxygenate and/or olefin-containing feedstock.

Due to this advantageous characteristic, there appears a possibility to increase the efficiency of the process for producing gasolines with improved antiknock rating due to more complete processing of all the components. The presence of water in the original raw mixture promotes the reduction in the coke deposition on the catalyst surface during its operation.

There is an embodiment, wherein a zeolite-containing catalyst is used, wherein a synthetic amorphous aluminosilicate or an inorganic oxide is used as a binder component, which is a mixture of alumina in an amount of 30-70 wt. % and silica in an amount of 70-30 wt. %. Due to this advantageous characteristic, there appears a possibility to increase the catalyst useful life, as there is no destruction of the binder under the action of superheated steam produced in the process of converting feedstock and present in the convertible feedstock.

There is an embodiment, wherein the catalyst is used which was described in RU 2160161 for the purposes of producing liquid hydrocarbons of dimethyl ether. In this embodiment the use of said catalyst is not restricted to the products and feeds indicated in the initial patent. This catalyst is based on crystalline pentasil-type aluminosilicate having a molar ratio of $SiO_2/Al_2O_3=25$-$100$ characterized by the presence of residual amounts of sodium ions being equivalent to a content of 0.05-0.1 wt. % of sodium oxide, containing said crystalline aluminosilicate and binder, wherein it further contains cobalt oxide, oxides of rare earth elements and zinc oxide in the following ratio, wt. %:

Zinc oxide: 0.5-3.0
Oxides of rare earth elements: 0.1-5.0
Cobalt oxide: 0.05-2.5
Crystalline aluminosilicate: 63-69.8
Binder: the rest.

Due to this advantageous characteristic, there appears a possibility to increase the octane characteristics of the produced gasoline due to increased formation of isoparaffins and alkylaromatics, primarily meta-xylene and p-xylene with BRON of 117.5 and 116.4, respectively, with the observed decrease in the concentration of benzene in the produced gasoline up to 0.5-1.0 wt. %, with a reduction in the olefin content of down to 1.5-2 wt. %, with a reduction in the content of dienes and trienes to trace amounts, with a reduction in the content of sulfur-containing compounds by 5 to 20 times, with simultaneous formation of hydrogen sulfide exhausted with gases.

There is an embodiment, wherein the catalyst is used which was described in RU 2544017 for the purposes of aromatization of $C_3$-$C_4$ gases, low octane hydrocarbon fractions and aliphatic alcohols, and mixtures thereof. In this embodiment the use of said catalyst is not restricted to the products and feeds indicated in the initial patent. Catalyst is based on the pentasil group zeolites, which contains a mechanical mixture of two zeolites having a different silicate module: zeolite having a $SiO_2/Al_2O_3=20$ previously treated with an aqueous solution of alkali modified with oxides of rare earth elements (REE) in an amount of 0.5-2.0 wt. %, and zeolite having $SiO_2/Al_2O_3=82$ having a residual amount of sodium oxide of 0.04 wt. % taken in the ratio of 1.7/1 to 2.8/1, and the remainder being a binder in an amount of 20 to 30 wt. % of the catalyst weight.

Due to this advantageous characteristic, there appears a possibility to expand the fractional composition of the converted hydrocarbon feedstock by including light hydrocarbon fractions.

There is an embodiment, wherein at least one reaction zone can contain zeolite-containing catalyst different from the catalysts in the other reaction zones.

Due to this advantageous characteristic, there appears a possibility to expand the fractional composition of hydrocarbon feedstock and to selectively enhance conversion of undesirable gasoline components accumulating in downstream reaction zones.

There is another possible embodiment of the invention, where the temperature of the last reaction zone is increased during the catalyst operation each time by 1-2° C. upon an increase in allowable values of methanol and/or oxygenates concentration in the reaction water.

Due to this advantageous characteristic, there appears a possibility to increase the methanol and/or oxygenates conversion degree (to increase efficiency of the conversion process) and reduce the costs of recycling the reaction water.

There is an embodiment, wherein olefin-containing gas is used as olefins, for example ethylene-containing gas from plants for fractioning of exhaust gas from the catalytic cracking process, gas from the delayed coking process, etc., to be used usually as a fuel. Due to this advantageous characteristic, there appears a possibility to increase the efficiency of use of olefin-containing feedstock.

There is a further embodiment, wherein the reaction zones are located in separate adiabatic reactors that are insulated reaction vessels filled with catalyst and connected in series.

There is a further embodiment, wherein the reaction zones are located in multi-bed adiabatic reactor.

There is a further embodiment, wherein the reaction zones are located in in multi-bed isothermal reactor.

There is a further embodiment, wherein the reaction zones are located in in multi-bed pseudo-isothermal reactor.

There is a further embodiment, wherein the reaction zones are located in separate reactors, each one of which can be adiabatic, isothermal or pseudo-isothermal.

In another embodiment, the flow rate of methanol and/or other oxygenates and/or olefin-containing feedstock into the reactor is increased or decreased upon deviation of the parameters of the produced product from the set parameters.

In another embodiment, the flow rate of methanol and/or other oxygenates and/or olefin-containing feedstock into individual reaction zones is increased or decreased upon deviation of parameters of the flows coming from individual reaction zones from the set parameters.

All this allows increasing the total useful volume of reactors of the simplest design up to hundreds of cubic meters and simplify their design, and allows increasing the volume of produced gasoline and improve its antiknock rating.

The totality of essential features of the proposed invention is not known from the prior art for methods for the similar purpose, which allows making a conclusion that the invention as a method complies with the "novelty" criterion.

Prior art of the plant Another aspect of the present invention relates to a plant for the production of gasolines from raw hydrocarbon fractions, fractions of gaseous olefins and oxygenates, comprising a unit (1) for supplying methanol and/or other oxygenates and/or olefin-containing feedstock, a unit (2) for supplying raw hydrocarbon fractions, a unit for supplying flows to be treated into a reactor, and a reactor (6) having at least a reaction zone with a zeolite-containing catalyst and an outlet for subsequent separation of the conversion product.

The closest by the technical essence plant (a prototype) is described in the Russian patent for invention No. 2429910 (publ. 27 Sep. 2011).

The disadvantage of the prototype is the lack of the ability to control the availability of heavy fractions in the hydrocarbon feedstock.

Another disadvantage of the described device is restrictions on fractional composition of feedstock. Thus, the description of prototype indicates that the feed-stock is supplied into the reactor in the gaseous phase at a temperature of no higher than 210° C., at the same time, the boiling point of n-octane reaches 233° C. at 1 MPa, which is by 23° C. higher than indicated in the prototype. Therefore, another drawback of the plant is the reduction of capabilities of the plant for processing feed-stock of various fractional composition.

Another drawback of the prototype invention is the limitation of the output of motor gasolines by limiting the possibility of increasing the volume of the reactor.

This is because the distance between the surfaces of the heat pipes limiting the volume of the reaction zone should not exceed 150 mm. The ratio of the reaction zone volume to the reactor volume will be less than 0.3-0.5. In addition, the reactor volume increases as the square of its diameter, and the required surface for heat pipes for heat removal increases in direct proportion to its diameter. This limits the development of a large-scale reactor fitted with heat pipes having a volume of dozens of cubic meters. Furthermore, as noted above, it is impossible to adjust the temperature of the end catalyst bed (in the last, boundary reaction zone) regardless of the temperature at the top reaction zone.

A further disadvantage of the prototype is also that upon an increase in the methanol to hydrocarbon ratio, the amount of heat generated in the front layer of the catalyst increases. This in turn limits the temperature of the temperature of heating the feedstock supplied into the reactor.

SUMMARY OF THE INVENTION AS A PLANT

The present invention also aims to propose a plant for producing gasolines from hydrocarbon fractions, fractions of gaseous olefins and oxygenates comprising a unit (1) for supplying methanol and/or other oxygenates and/or olefin-containing feedstock, a unit (2) for supplying raw hydrocarbon fractions, a unit for supplying flows to be treated into a reactor, and a reactor having at least a reaction zone with a zeolite-containing catalyst and an outlet for subsequent separation of the conversion product, wherein this plant allows at least mitigating the above drawback, namely, providing the improvement in the quality of the resulting gasoline due to reducing its benzene content, as well as content of high melting point components, such as durene, as well as due to the possibility of regulating the temperature throughout the catalyst bed without using a complicated heat-exchange reactor equipment, and the ability to increase the useful volume of the reactor equipment, which is the specified technical problem.

To achieve this objective, the reactor is additionally provided with at least one more reaction zone, and the unit for supplying flows into the reactor is adapted to supply separate and/or pre-mixed flows of methanol and/or other oxygenates and/or olefin-containing feedstock and the flow of raw hydrocarbon fractions into the first reaction zone, and a flow of methanol and/or other oxygenates and/or olefin-containing feedstock into the second and/or subsequent reaction zone, wherein between the reaction zones, there is also located means for mixing the reaction products from the upstream reaction zone and supplied methanol and/or other oxygenates and/or olefin-containing feedstock.

Due to these advantageous characteristics, there appears a possibility to improve the quality of produced gasoline due to the reduction in the content of benzene and high melting point components such as durene in produced gasoline. Additionally, it becomes possible to adjust the temperature throughout the catalyst bed without using complicated heat-exchange reactor equipment.

Furthermore, it is possible to increase production of gasolines due to the possibility of increasing the volume of the reactor. Indeed, the use of a reactor with at least two reaction zones with methanol and/or other oxygenates and/or olefin-containing feedstock being supplied into each or at least two reaction zone allows increasing the production capacity due to the possibility of increasing the total volume of the reactor. Here, the reaction zones can be arranged in series in the vertical or horizontal direction.

In one of the embodiments, the unit for supplying flows contains a unit (5) for heating methanol and/or other oxygenates and/or olefin-containing feedstock, which has at least two outputs, the first of which is connected to the first input of the first reaction zone (61) directly or through the mixing zone, the second input of which is connected to the output of a unit (2) for supplying raw hydrocarbon fractions, wherein through the second output of the unit (5) there is supplied a flow of methanol and/or other oxygenates and/or olefin-containing feedstock to the second reaction zone. Here, the unit for supplying flows contains an additional heating unit (4), the input of which is connected to the output of the unit (2) for supplying raw hydrocarbon fractions directly, and the output is connected to the second input into the first reaction zone (61).

In one of the embodiments, the unit for supplying flows contains a unit (5) for heating methanol and/or other oxygenates and/or olefin-containing feedstock, which has at least two outputs, the first of which is connected to the first input of the first reaction zone (61) directly or through the mixing zone, the second input of which is connected to the output of a unit (2) for supplying raw hydrocarbon fractions, wherein through the second output of the unit (5) there is supplied a flow of methanol and/or other oxygenates and/or olefin-containing feedstock to the third reaction zone. Here, the unit for supplying flows contains an additional heating unit (4), the input of which is connected to the output of the unit (2) for supplying raw hydrocarbon fractions directly, and the output is connected to the second input into the first reaction zone (61).

In another embodiment, the unit for supplying flows contains a unit (5) for heating methanol and/or other oxygenates and/or olefin-containing feedstock having at least one output connected to the input into the second and/or subsequent reaction zone directly or through the mixing zone comprising means for mixing located between the reaction zones, and a unit (3) for mixing raw hydrocarbon fractions and methanol and/or other oxygenates and/or olefin-containing feedstock, whose output is connected to the input to the first reaction zone, directly or through an additional heating unit (4).

In another embodiment, the unit for supplying flows contains a unit (5) for heating methanol and/or other oxygenates and/or olefin-containing feedstock having at least one output connected to the input into the third reaction zone directly or through the mixing zone comprising means for mixing located between the reaction zones, and a unit (3) for mixing raw hydrocarbon fractions and methanol and/or other oxygenates and/or olefin-containing feedstock, which has at least two outputs which are connected to the inputs of the first and second reaction zones, directly or through an additional heating unit (4).

Means for mixing hydrocarbon fractions and oxygenates can be located upstream the first reaction zone.

In yet another embodiment, the plant further contains a unit (10) for determining parameters of produced gasoline connected to a unit (11) controlling the flow rate of methanol and/or other oxygenates and/or olefin-containing feedstock, with which is additionally provided a unit (1) for supplying methanol and/or other oxygenates and/or olefin-containing feedstock.

In yet another embodiment, the plant further contains a unit (10) for determining parameters of flow produced after individual reaction zones connected to a unit (11) controlling the flow rate of methanol and/or other oxygenates and/or olefin-containing feedstock, with which is additionally provided a unit (1) for supplying methanol and/or other oxygenates and/or olefin-containing feedstock.

There is an embodiment, wherein the unit (4) for heating raw hydrocarbon fraction further includes a unit for evaporating raw hydrocarbon fractions or mixtures of raw hydrocarbon fractions and methanol and/or other oxygenates and/or olefin-containing feedstock and a unit for heating, e.g., preferably superheating, the formed vapors, wherein between them there is a separator for removal of heavy hydrocarbon fractions containing mainly hydrocarbon components with a molecular mass of no more than 180, with boiling point temperatures of up to 250° C. under normal conditions.

Due to this advantageous characteristic, in an embodiment using a superheater, there appears a possibility to reduce the content of heavy high-boiling components in gasoline and reduce the coking rate of the catalyst, reduce potential coke deposition on the inner surfaces of the raw hydrocarbon heater, in an embodiment superheater.

There is another embodiment, wherein a mixing device for mixing the reaction products of the upstream reaction zone and supplied methanol and/or other oxygenates and/or olefin-containing feedstock is made as a bed of granules of a neutral material and/or a fraction of crushed quartz placed upstream the front catalyst bed.

Due to this advantageous characteristic, there appears a possibility to use the protective bed of granules of a neutral material and/or a fraction of crushed quartz placed upstream the front catalyst bed as a device for mixing the reaction products from the upstream reaction zone and supplied methanol and/or other oxygenates and/or olefin-containing feedstock.

There is also an embodiment, wherein a line connecting the reaction zones (reactor spaces in which the reaction zones are located) is used as a mixing device for mixing the reaction products of the upstream reaction zone and supplied methanol and/or other oxygenates feedstock and/or olefin-containing feedstock.

Due to this advantageous characteristic, there appears a possibility to use the line connecting the reaction zones as a device for mixing the reaction products of the upstream reaction zone and supplied methanol and/or other oxygenates and/or olefin-containing feedstock.

In one of the embodiments, function of a mixing device is carried out by a protective bed of neutral or weakly-reacting material, for example quartz, in forms such as granules; spheres; fraction of crushed materials.

In one of the embodiments, function of a mixing device is carried out by a channel connecting the reactor spaces where the reaction zones are located.

In one of the embodiments, function of a mixing device is carried out by specifically controlled speed and/or direction of supplied feedstock flow, e.g. by using tangential supply of methanol and/or other oxygenates and/or olefin-containing feedstock to the reaction zone.

There is also an embodiment, wherein some or all the reaction zones are made as separate adiabatic reactors, which are thermally insulated reaction vessels filled with catalyst and connected in series.

There is a further embodiment, wherein the reaction zones are located in multi-bed adiabatic reactor.

There is a further embodiment, wherein the reaction zones are located in in multi-bed isothermal reactor.

There is a further embodiment, wherein the reaction zones are located in in multi-bed pseudo-isothermal reactor.

There is a further embodiment, wherein the reaction zones are located in separate reactors, each one of which can be adiabatic, isothermal or pseudo-isothermal.

Due to this advantageous characteristic, there appears a possibility to increase the maximum useful volume of the used reactor equipment and therefore increase the production of gasolines.

There is an embodiment, wherein upstream the last one or two reaction zones, there are located raw mixture heaters, e.g., preferably superheaters.

Due to this advantageous characteristic, there appears a possibility to use the proposed invention at a low flow rate of methanol per metric ton of convertible hydrocarbon feedstock. Indeed, at low flow rates of methanol less than 20% of weight of the converted feedstock, to enhance RON of converted mixtures the proposed combined embodiment can be used, wherein a reaction mixture heater, e.g., preferably superheater, heating the reaction mixture up to temperatures of about 500° C. is located upstream the last or the penultimate and the last reaction zones. Additionally, there appears a possibility to raise the temperature in the reaction zones as the catalyst is deactivated to improve the efficiency of conversion of hydrocarbon feedstock and oxygenates.

There is also an embodiment, wherein the plant further contains a conversion product separation unit for removal of the reaction water with an admixture of methanol and/or other oxygenates, whose output is connected to the input of a rectification column, the distillation residue of which is water cleaned from residues of hydrocarbons with a reduced content of oxygenates, and the distillate of which are hydrocarbons and water with an increased content of oxygenates, wherein the distillation column output with the distillate is connected to the input of the unit for supplying methanol and/or other oxygenates and/or olefin-containing feedstock.

Due to this advantageous characteristic, there appears a possibility to increase the efficiency of gasolines production process due to a more complete processing of all components.

The totality of essential features of the proposed invention is not known from the prior art for a device for the similar purpose, which allows making a conclusion that the invention as a unit complies with the "novelty" criterion.

BRIEF DESCRIPTION OF THE DRAWINGS

Other features and advantages of the invention clearly emerge from the description that is given below for illustration and is non-limiting, with reference to the accompanying drawings, where.

Figure 1:
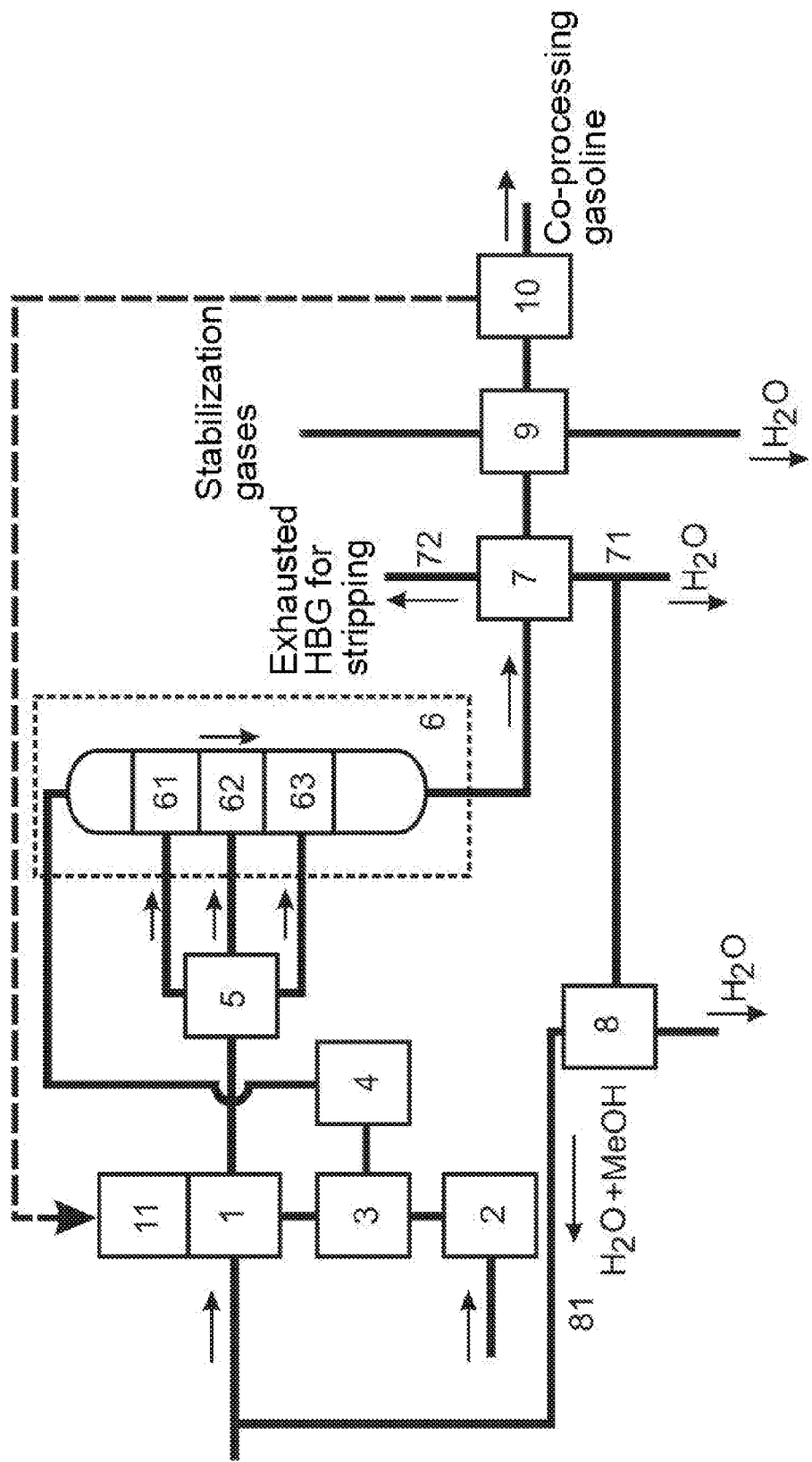
FIG. 1 schematically shows a general view of a plant for producing gasoline from raw hydrocarbon fractions according to the invention, wherein the unit for supplying flows contains a unit (5) for heating methanol and/or other oxygenates and/or olefin-containing feedstock having at least two outputs (an embodiment, wherein said unit has at least one outlet, is not shown in the drawings)
Figure 2:
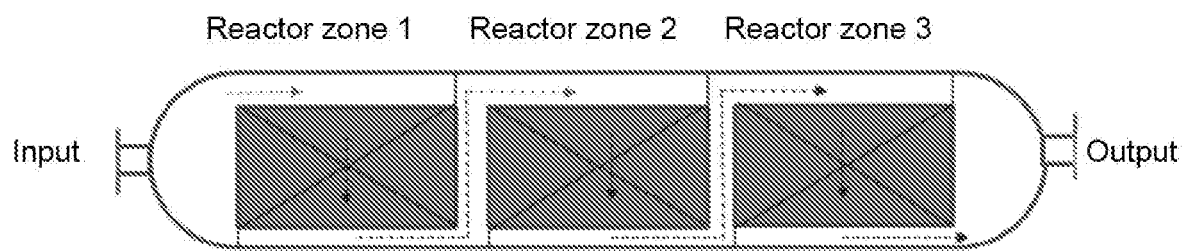
FIG. 2 shows a horizontal multiple-shell reactor.

According to FIG. 1, a plant for production of a base stock for production of gasoline from raw hydrocarbon fractions, fractions of gaseous olefins and oxygenates includes a unit 1 for supplying methanol and/or other oxygenates and/or olefin-containing feedstock, and a unit 2 for supplying raw hydrocarbon fractions, whose outputs are connected to inputs of a unit 3 for mixing starting components, the output of which is connected to the input of a unit 4 for heating the feedstock (raw hydrocarbon fractions or mixtures thereof with methanol and/or other oxygenate and/or olefin-containing feedstock), whose output is connected to the inlet of a reactor 6, in which the reaction is carried out in the presence of a zeolite-containing catalyst, whose output is connected to the input of a unit 7 for separating the conversion product having the output 71 for removal of the reaction water and the outlet 72 for flue gases exhaust.

The reactor 6 is made as a multiple-shell reactor that includes reaction zones on each shelf/catalyst basket or as a horizontal reactor, the housing of which accommodates several series-connected catalyst baskets. Either every reaction zone, or part of the reaction zones may be made as individual thermally insulated vessels.

The unit 1 for supplying methanol and/or other oxygenates and/or olefin-containing feedstock is connected to the unit 5 for heating the unit for supplying flows. The unit 5 may have at least one or at least two outputs.

In case of at least one outlet (not shown in the drawings), said output is connected to the input to the second reaction zone 62 either directly or through the mixing zone having means for mixing located between the reaction zones, wherein the unit for supplying also contains a unit 3 for mixing the starting components, whose output is connected to the inlet to the first reaction zone 61 either directly or through the heating unit 4. In the proposed embodiment, the downstream (second) output of the unit 5 may also be connected to the inlet to the first reaction zone 61 (FIG. 1) directly or through the mixing zone.

In case of at least two outputs (FIG. 1), one of which is connected to the first input of the first reaction zone 61 either directly or through the mixing zone, the second input in which is connected to the output of the unit 2 for supplying raw hydrocarbon fractions, wherein through the second output of the unit 5 the flow is supplied to the second reaction zone 62.

The separation unit 7 is connected to gasoline stabilization column 9, wherein the bottom product is stabilized gasoline with improved antiknock rating. Other products of the column are gasoline stabilization gases and reaction water trapped out of the column reflux tank.

Upstream the reaction zones, the plant further includes a mixing device installed for mixing the reaction products from the upstream reaction zone and supplied methanol and/or other oxygenates and/or olefin-containing feedstock. The mixing device is not shown in FIG. 1.

In one of the embodiments, a mixer for mixing the reaction products from the upstream reaction zones and supplied methanol and/or other oxygenates and/or olefin-containing feedstock is made as a bed of granules of neutral material and/or a fraction of crushed quartz placed upstream the front catalyst bed, and a line connecting the reaction zones is used as a mixing device.

The plant further may include devices for heating the reaction mixture installed upstream the last or the penultimate and last reaction zones; the diagram of FIG. 1 does not show the heating devices.

The last one or two reaction zones of the reactor can be made as isothermal reactors.

The plant further includes a unit 10 for determining the parameters of the resulting gasoline, such as RON, connected to a unit 11 controlling the flow rate of methanol and/or other oxygenates and/or olefin-containing feedstock in the unit 1 for supplying methanol and/or other oxygenates and/or olefin-containing feedstock.

The plant further includes a reaction water distillation column 8, the bottom product of which is water cleaned of residues of hydrocarbons with a reduced content of methanol and/or other oxygenates, and the distillate of which is water with an increased content of methanol and/or other oxygenates and hydrocarbons.

The output of the conversion product separation unit for removal of the reaction water with an admixture of methanol can be connected to the input of the rectification column 8, wherein the output of the distillation column with distillate is connected to the input of the unit 1 for supplying methanol and/or other oxygenates and/or olefin-containing feedstock.

EMBODIMENT OF THE INVENTION

Figure 3:
FIG. 3 schematically depicts the steps of a process for producing gasolines from raw hydrocarbon fractions according to the invention.

The gasoline base of raw hydrocarbon fractions, fractions of the gaseous olefins and oxygenates is produced as follows (see FIGS. 1, 3).

Step A1. In the unit 3, starting components are mixed, which are supplied through the unit 1 for supplying methanol and/or other oxygenates and/or olefin-containing feedstock, and the unit 2 for supplying raw hydrocarbon fractions.

Step A2. The starting feedstock is heated in the unit 4 for heating the starting feedstock. During heating, if necessary, the heavy components are separated.

Step A3. The mixture is supplied from the unit 4 to the reactor 6, wherein the reaction is carried out in the presence of a zeolite-containing catalyst. The reactor contains at least two reaction zones, where the zeolite-containing catalyst is located. The mixture from step A2 is supplied into the first reaction zone 61. After heating in the unit 5, methanol and/or other oxygenates and/or olefin-containing feedstock are divided into several flows, the first flow is mixed with the converted hydrocarbon feedstock from the first reaction zone 61 in the mixing zone between the first and second reaction zones, and the subsequent flows are mixed in the downstream mixing zones (not shown in the drawings) with the conversion product from the upstream reaction zone.

A bed of granules of a neutral material and/or a fraction of crushed quartz placed upstream the catalyst bed placed on a shelf, or a line connecting the reaction zones are used as a mixing zone (a mixing device).

Methanol and/or other oxygenates are supplied in the gaseous phase at a temperature of no more than 380° C. preventing its decomposition upon heating.

The isothermal reactors are used as the last or the last and the penultimate reaction zones of the reactor. Alternatively, the adiabatic reactors are used as the last or last and the penultimate reaction zones of the reactor.

Zeolite-containing catalysts are used in the reaction zones, whose binder is a mixture of alumina in an amount of 30-70 wt. % and silica in an amount of 70-30 wt. %.

Alternatively, the catalyst is used for production of liquid hydrocarbons of dimethyl ether based on crystalline pentasil-type aluminosilicate having a molar ratio of $SiO_2/Al_2O_3=25-100$ characterized by the presence of residual amounts of sodium ions equivalent to a content of 0.05-0.1% wt. of sodium oxide containing said crystalline aluminosilicate and binder, wherein it further contains cobalt oxide, oxides of rare earth elements and zinc oxide at the following component ratio, wt. %:

Zinc oxide: 0.5-3.0
Oxides of rare earth elements: 0.1-5.0
Cobalt oxide: 0.05-2.5
Crystalline aluminosilicate: 63-69.8
Binder: the rest.

Alternatively, the catalyst of light aliphatic hydrocarbon conversion is used characterized in that a mixture of pentasil group zeolites with a different silicate module is used as the HZSM-5 zeolite: 1) zeolite with $SiO_2/Al_2O_3=20$ previously treated with an aqueous solution of alkali, modified with oxides of rare earth elements (REE) in an amount of 0.5-2.0 wt. %, and 2) zeolite with $SiO_2/Al_2O_3=82$ with a residual amount of sodium oxide in an amount of 0.04 wt. % taken in a ratio of 1.7/1 to 2.8/1, and the remainder being a binder in an amount of 20 to 30 wt. % of the catalyst.

Step A4. The flow rate of methanol and/or other oxygenates and/or olefin-containing feedstock into the reaction zones is controlled (by the unit 1 and through picking methanol and/or other oxygenates and/or olefin-containing feedstock into the reaction zone from the unit 5), and the temperature of the mixture supplied to the first reaction zone (by the unit 4) is controlled so that the maximum temperature of the catalyst bed does not exceed 420° C. in the preparation of the base stock for the production of high-octane gasoline and 500° C. for the production of a concentrate alkylaromatics, and the temperature of the end catalyst bed in the reaction zone is respectively by 40-70° C. below the maximum temperature of the bed. If methanol is supplied in an amount of less than 20 to 25 wt. %, additional heat supply to the downstream reaction zones is required. To supply heat, hot stabilization gases from the fractionation unit 9 or heated circulating exhaust gases from the unit 7 can be used, or a heater can be installed on the line connecting 2 last zones, or heat is supplied using the heat pipes, or otherwise, or heat supply can be carried out through heating, e.g., preferably superheating the flow supplied into the last or the last and the penultimate reaction zones, but no more than up to 500° C., or isothermal reaction zones with heat exchanging heat supply can be used as the last or the last and the penultimate reaction zones.

Step A5. The temperature of the last or the last and the penultimate reaction zones is decreased during catalyst operation each time by 1-2° C. as the allowable concentration of methanol in the reaction water increases. FIG. 1 does not show a schematic drawing of additional heat supply to the last or the last and the penultimate reaction zones to control the temperature in this zone. To supply heat, heated stabilization gases from the fractionation unit 9 or circulating heated exhaust gases from the unit 7 can be used, or a heater can be installed on a line connecting the last 2 zones, or heat is supplied through the heat pipes or using other means.

Step A6. A 1-2% aqueous solution of an industrial demulsifier is added to a mixture of hydrocarbons and water supplied to the separation at a ratio of 1:100-1:200 to the volume of the reaction water. Here, the aqueous solution of the demulsifier is mixed with the input flow in a laminar static mixer or directly in a condenser of hydrocarbons and reaction water located in the separation unit 6 upstream a three-phase separator.

Step A7. Gasoline is isolated by the separation of the conversion product while diverting simultaneously the reaction water and exhaust gases.

In the unit 7, the reaction mixture is cooled with partial condensation of $C_5+$ hydrocarbons and the aqueous portion, further, the three-phase separator located in the same location separates the mixture into the gaseous phase, hydrocarbon condensate and reaction water. The separated hydrocarbon condensate is supplied to a distillation unit 9, from where gasoline selected by stabilized vapor pressure and dried is picked up, and stabilization gases and reaction water with a high content of methanol are picked up from the reflux tank. The separated reaction water with an admixture of methanol and/or other oxygenates is supplied to the distillation unit 8, the distillation residue of which is water cleaned of residues of hydrocarbons with a reduced content of methanol and/or other oxygenates, and the distillate of which is water with a higher content of methanol and/or other oxygenates and hydrocarbons, wherein water with an increased content of oxygenates and hydrocarbons produced in the rectification process are recycled to the reactor inlet to the beginning of the process in a mixture with methanol and/or other oxygenate and/or olefin-containing feedstock.

Step A8. If the parameters of the produced gasoline with improved antiknock rating differ from the specified parameters that are measured by the unit 10 for determining the parameters of the resulting gasoline, the flow rate of methanol and/or other oxygenates and/or olefin-containing feedstock to the reactor is increased or decreased by the unit 11 controlling the flow rate of methanol and/or other oxygenates and/or olefin-containing feedstock.

The sequence of steps is exemplary and allows rearranging, adding or making some operations simultaneously without losing the ability of the production of a base stock for the production of gasolines from raw hydrocarbon fractions, fractions of gaseous olefins and oxygenates.

INDUSTRIAL APPLICABILITY

The proposed plant for producing gasolines from raw hydrocarbon fractions can be embodied in practice, and upon embodiment, it provides an implementation of the declared application, which allows making a conclusion that the invention complies with the "industrial applicability" criterion.

In accordance with the proposed invention, tests and calculations for the production of gasolines from various hydrocarbon fractions, fractions of gaseous olefins and oxygenates have been conducted.

Example No. 1. Modeling the First Reaction Zone

A zeolite catalyst was used for the conversion of dimethyl ether after regeneration.

The process was carried out at atmospheric pressure in a reactor having a useful volume of about 1.5 liters and with thermal insulation made as an air gap between the external surface of the cylindrical reactor shell and an outer protection casing, and with compensation of heat losses using external heating of the protective casing. Previously, the catalyst bed having a volume of 1.2 liters (855 g) was heated to a temperature of 350° C. A mixture of the following mass composition was supplied on the catalyst bed at a temperature of 335° C.:
Methanol: 6.6%
Water: 7%,
Ethylene: 2.9%, and
Straight-run hydrocarbon fraction: 65-85° C., 83.4%, with the composition given in Table 3.

The mass feedstock flow rate was 2.6 kg/L of catalyst·h$^{-1}$. During steady state, the temperature of heating of the adiabatic catalyst bed in a narrow front bed (no more than one quarter of the charged catalyst) was about 60-65° C. (from 335° C. to 395-398° C.)), the end catalyst bed temperature was about 360° C.

The mass yield of the $C_5+$ fraction from the first reaction zone was 97.5% per the hydrocarbon fraction supplied (65-85° C.). RON for the $C_5+$ hydrocarbons fraction to be released from the conversion products was 67 units with RON of the initial fraction equal to 58 units. The methanol conversion was 99.9%.

Example No. 2. Increase in RON of the Product by Increasing the Methanol Flow Rate It differs from the Example No. 1 by that the temperature of the raw mixture was reduced down to 320° C. A mixture of the following mass composition was supplied to the reactor inlet:
Methanol: 10.7%
Water: 3.4%
Ethylene 2.6%, and
Fraction, 65-85° C.: 83.4% the rest.

The mass feedstock flow rate was 2.6 kg/L of catalyst·h$^{-1}$. During steady state, the temperature of heating of the adiabatic catalyst bed in a narrow front bed (less than one quarter of the charged catalyst) was about 80-85° C. (from 320° C. to 402-406° C.)), the end catalyst bed temperature was about 365° C. The mass yield of the $C_5+$ fraction from the first reaction zone was 96.4% per the hydrocarbon fraction supplied (65-85° C.). RON for the $C_5+$ hydrocarbons fraction to be released from the conversion products was 71 units with RON of the initial fraction equal to 58 units. The methanol conversion was 99.5%.

Example No. 3

We used the same catalyst as that used in experiment 1. A flow reactor was used, wherein the catalyst was filled for the conversion of light hydrocarbons and oxygenates to aromatics concentrate in three beds in an amount of 18 ml of the catalyst each (a total amount of 40 g of catalyst). The catalyst beds were separated by quartz chip beds in an amount of 36 ml each forming the zones for mixing and heating the hydrocarbon feedstock. A narrow straight-run gasoline fraction at 65-85° C. having a density of 0.71 at a flow rate of 60 ml/hr and 80 wt. % methanol at a flow rate of 12 ml/hr were supplied to the first reaction zone.

Additionally, 80 wt. % methanol was supplied through the capillaries at a rate of 6 ml/hr to the second and third reaction zones through the mixing zones. The ratio of methanol/straight-run fraction was equal to 0.38.

Temperature in the reaction zones: 365-380° C.
Reactor pressure: 0.3-0.35 MPa.

Material balance of experiment as of the 4$^{th}$ hour of the experiment is given in the Table below.

TABLE 1

| Supplied | g/hr |
|---|---|
| to the first reaction zone | |
| Fraction 65-85° C. (RON 58) | 42.7 |
| Methanol | 8.13 |
| Water | 2.03 |
| To the second reaction zone additionally | |
| Methanol | 4.065 |
| Water | 1.01 |
| To the third reaction zone additionally | |
| Methanol | 4.06 |
| Water | 1.015 |
| Total supplied | 62.98 |

TABLE 1-continued

| Supplied | g/hr |
|---|---|
| Produced | |
| Liquid fraction of hydrocarbons (RON 87.5) | 41.8 |
| Reaction water | 13.21 |
| Hydrocarbon hydrogen-containing gas having a propane content of up to 39 wt. % | 7.97 |
| Conversion of methanol | 99.7% |
| $C_5$+ hydrocarbon yield per gasoline supplied | 0.975 |

Example No. 4 (Comparative)

A flow reactor was loaded with 36 ml (26.7 g) of the catalyst, where a narrow straight-run gasoline fraction at 65-85° C. having a density of 0.711, at a flow rate of 36 ml/hr and 100 wt. % methanol at a flow rate of 12 ml/hr were supplied.

The ratio of methanol/straight fraction was equal to 0.371.

The temperature in the reaction zone was 365-380° C.

The reactor pressure was 0.3-0.35 MPa.

The material balance as of the 4$^{th}$ hour of the experiment is shown in Table 2.

TABLE 2

| Supplied | g/hr |
|---|---|
| Fraction at 65-85° C. (RON 58) | 25.60 |
| Methanol | 9.50 |
| Total supplied | 35.10 |
| Produced | |
| Liquid fraction of hydrocarbons (RON 86.3) | 24.79 |
| Reaction water | 5.34 |
| Hydrocarbon hydrogen-containing gas having a propane content of up to 42 wt. % | 4.97 |
| Conversion of methanol | 100% |
| $C_5$+ hydrocarbon yield per gasoline supplied | 0.968 |

Table 3 shows a comparison of the compositions in weight percentage of the initial narrow straight-run fraction $C_6$-$C_7$, and $C_5$+ hydrocarbon fraction from the catalysate hydrocarbon condensate. As seen from the comparison of examples when using a reactor with three reaction zones and with the distributed supply of methanol, the benzene and durene content in gasoline reduced, the content of alkylaromatics increased.

TABLE 3

| Component description | Feedstock (fraction at 65-85° C.) | $C_5$+ fraction from catalysate hydrocarbon condensate, Example 4 (comparative) | $C_5$+ fraction from hydrocarbon condensate, Example 3 (reactor with 3 reaction zones) |
|---|---|---|---|
| $C_5$-$C_6$ olefins | | 0.20% | 0.32% |
| Sum of $C_6$-$C_8$ five-membered naphthenes | 9.26% | 8.18% | 8.40% |
| Sum of $C_6$-$C_8$ six membered naphthenes | 5.97% | 3.79% | 2.82% |
| Isopentane | 0.00% | 3.91% | 4.22% |
| Sum of $C_6$ isoparaffins with two branches | 0.49% | 1.03% | 1.16% |
| Sum of $C_7$ isoparaffins with two branches | 29.33% | 22.18% | 20.51% |
| Sum of $C_6$ isoparaffins with one side branch | 9.34% | 11.26% | 11.53% |
| Sum of $C_7$ isoparaffins with one side branch | 15.69% | 6.04% | 6.38% |
| n-pentane | | 3.44% | 3.78% |
| n-hexane | 20.93% | 9.71% | 9.52% |
| n-heptane | 6.57% | 1.66% | 1.51% |
| Benzene | 1.53% | 1.12% | 0.76% |
| Toluene | 0.90% | 5.29% | 4.55% |
| Xylenes and ethylbenzene | | 11.31% | 12.69% |
| $C_9$ aromatics | | 6.79% | 7.55% |
| $C_{10}$ aromatics | | 3.10% | 2.85% |
| $A_{11}$+ | | 1.12% | 1.45% |
| Total | 100% | 100% | 100% |
| Including aromatics | 2.4% | 28.70% | 30.10% |
| Including sum of tetra-methylbenzenes | | 1.20% | 0.93% |
| Of these, durene (1,2,4,5-tetramethylbenzene) | | 0.46% | 0.30% |

Example No. 5

This example demonstrates the possibility of using feedstock containing diene and triene hydrocarbons, as well as the ability to control the degree of conversion of feedstock by increasing the maximum process temperature.

A catalyst of conversion of light aliphatic hydrocarbons was used.

The feedstock was a mixture consisting of a mixture of SNG (stable natural gasoline) in an amount of 50 vol. % and a light fraction (initial boiling point: 120° C.) of catalytic cracking gasoline from Ufa Refinery. The total sulfur content in the mixture fraction was 0.008 wt. %. The content of diene and triene hydrocarbons was 0.3 wt. Into a flow reactor, 100 ml. (74 g) of fresh catalyst was loaded. During the experiment, to maintain RON at a level of about 92 units the volumetric feed-stock flow rate was reduced by 20%, and the maximum temperature in the reaction zone was increased from 380 to 390° C.

Table 4 shows the material balance of the experiment corresponding to the 203$^{rd}$ hour of the pilot plant operation. Diene and triene hydrocarbons were not detected in the produced gasoline. The total sulfur content was reduced to 0.001 wt. %. The methanol conversion during the experiment was no less than 99% and was adjusted by increasing the temperature in the reaction zone and reducing the feedstock volumetric flow rate.

TABLE 4

| Supplied | g/hr |
|---|---|
| Mixture of 50% of SNG and light fraction catalytic cracking gasoline (initial boiling point: 120° C.). | 50.47 |
| Methanol | 23.73 |
| Total supplied | 74.20 |
| Produced | |
| Liquid fraction of hydrocarbons (RON 92) | 44.90 |
| Reaction water | 13.39 |

TABLE 4-continued

| Supplied | g/hr |
| --- | --- |
| Hydrocarbon hydrogen-containing gas having a propane content of up to 55 wt. % | 15.9 |
| Methanol conversion | 100% |

Example No. 6 (Calculated)

The content of methanol in the reaction water is 1.3 wt. %.

The reaction water is supplied into an evaporator with a vapor space where it is evaporated at a pressure close to atmospheric pressure. Vapors of the reaction water are supplied to a column still. The number of fractionating trays in the column is ten. Vapors from the top of the column are condensed and supplied partially as reflux to the column for reflux. The yield of distillate is 11 wt. % of the weight of the starting feedstock supplied to the column as vapor. The concentration of methanol in the distillate is 8-9 wt. %. This product is admixed to 100 wt. % methanol supplied for conversion together with the hydrocarbon feedstock. As a result, methanol at a concentration of 94 wt. % is supplied for conversion. The bottom product of the column is desalted and water cleaned of hydrocarbons, with the methanol content of no more than 0.2 wt. %.

Thus, as a result of measurement and calculations, it has been found that the separation of methanol and/or other oxygenates and/or olefin-containing feed-stock into multiple flows according to the invention with simultaneous utilization of a reactor comprising at least two reaction zones, allows increasing the useful reactor volume, simplify its design, and besides reduce gassing, reduce the consumption of methanol per unit of increment of RON of the base stock for the production of gasolines.

Accordingly, the present invention achieves the task set, i.e. increasing the quality of the produced high-octane gasoline due to the reduction of the content of benzene in gasoline, as well as the content of high melting point components such as durene, as well as due to the possibility of regulating the temperature throughout the catalyst bed without using complicated heat-exchange reactor equipment, as well as the possibility of increasing the useful volume of reactor equipment.

An additional advantage of the proposed solution is that:
There is a low content of $C_1$-$C_2$ hydrocarbons in exhaust gases, and since hydrogen is substantially insoluble in liquid hydrocarbons, this allows producing hydrogen-containing gas by using the $C_{3+}$ hydrocarbon absorption from exhaust gases with debutanized gasoline from the discussed plant.

Instead of a factory gas fractioning plant, an absorption column can be used, into which gasoline is supplied that has been produced in the plant and cooled down to a temperature range of −10° C. to +15° C. Saturated gasoline is supplied from this column to the stabilization column (unit 9). This increases the yield of commercial propane-butane mixture ($C_3$-$C_4$) and allows producing hydrogen-containing gas with a low hydrocarbon content.

As feedstock for the production of gasoline, instead of straight-run gasoline or in conjunction with it, there can be used side-cut fractions from various processes, including fractions containing benzene and so on, fractions containing diene hydrocarbons, including light catalytic cracking gasolines.

Sulfur content in co-processed gasoline is 5-20 times lower than that in the original gasoline. This is because the catalyst runs on feedstock having a sulfur content in convertible gasoline of up to 500 ppm by weight. Sulfur is mainly trapped out as hydrogen sulfide along with exhaust gases and is partly sorbed on the catalyst and is removed during regeneration.

Gasolines produced in the processing by their basic characteristics (group composition, RON, sulfur content, etc.) comply completely with the fifth grade gasoline characteristics in terms of technical regulations under the Customs Union (CU TR 013/2011) "On requirements for automobile and aviation gasoline, diesel and marine fuel, jet fuel and heating oil".

The various embodiments of feedstocks, materials, processes, methods, equipment, and systems, set forth in this specification may be used may be used with each other in different and various combinations. Thus, for example, the configurations provided in the various embodiments of this specification may be used with each other; and the scope of protection afforded the present inventions should not be limited to a particular embodiment, configuration or arrangement that is set forth in a particular embodiment, example, or in an embodiment in a particular Figure.

Although the present invention has been described in detail by exemplary embodiments, which appear to be preferred ones, it should be remembered that these embodiments are given only for the purpose of illustrating the invention. This description should not be construed as limiting the scope of the invention, since the steps of the described methods and plants may be amended by experts in the field of oil, petrochemicals, physics, etc. in order to adapt them to specific plants or situations, and not leaving the scope of the appended claims. Those skilled in the art will understand that within the scope of the invention as defined by the claims, various variations and modifications, including equivalent solutions, are possible.

The invention claimed is:

1. A method of producing gasoline, the method comprising:
    a. heating a first feed stream to a predetermined temperature;
    b. supplying the first feed stream, the first feed stream comprising a raw hydrocarbon fraction at the first predetermined temperature to a reactor comprising a first reaction zone in fluid communication with a second reaction zone, the first reaction zone and the second reaction zone comprising a zeolite catalyst, whereby a first conversion product provided from the first reaction zone is supplied to the second reaction zone, the second reaction zone providing a second conversion product;
    c. supplying a second feed stream, the second feed stream comprising one or more of methanol, ethanol, other oxygenates, and olefins, heating and separating the second feed stream, whereby the second feed stream is heated to a second predetermined temperature and separated into a first flow and a second flow;
    d. wherein the first flow is supplied into the first reaction zone; and the second flow is supplied into the second reaction zone; and,
    e. the reactor providing a final conversion product to a separation unit, wherein the final conversion product is separated into a hydrocarbon condensate stream and a reaction water stream.

2. The method of claim 1, wherein the second feed stream consists essentially of an oxygenate and the olefin.

3. The method of claim 1, wherein the temperature of the first reaction zone, the second reaction zone, or both is regulated without using heat exchange equipment.

4. The method of claim 1, wherein the temperature of the reactor is regulated without using a heat-exchanger.

5. The method of claim 1, wherein the temperature of the first reaction zone is controlled by feed rates and temperatures of the first feed stream and first flow; whereby the temperature of the first reaction zone is controlled without the using heat-exchangers.

6. The method of claim 1, wherein the temperature of the second reaction zone is controlled by feed rates and temperatures of the first conversion product and second flow; whereby the temperature of the second reaction zone is controlled without the using heat-exchangers.

7. The method of claim 1, wherein the method additionally comprises distilling water from the reaction water stream, whereby a concentration of one or more of methanol, oxygenates, and hydrocarbons is increased, thereby providing a concentrated reactions water stream; and recirculating the concentrated reaction water stream into a zone of the reactor.

8. The method of claim 7, comprising a control unit that controls a rate of recirculating the concentrated reaction water stream into the reactor to thereby control the temperature of the reactor.

9. The method of claim 1, comprising supply the first feed stream to a separation steps, wherein heavy hydrocarbon fractions are removed from the first feed stream prior to supplying the first feed stream to the reactor, whereby hydrocarbon components of the first feed stream entering the reactor have a molecular mass of no more than 180 and a boiling point of no more than 250° C., thereby reducing coking of the catalyst.

10. The method of claim 1, wherein the first reaction zone, the second reaction zone, or both, are adiabatic reactors.

11. The method of claim 1, wherein the first reaction zone, the second reaction zone, or both, are thermally insulated reaction zones.

12. The method of claim 1, wherein the first reaction zone, the second reaction zone, or both, are isothermal reaction zones.

13. The method of claim 1, wherein the first predetermined temperature is no more than 500° C.

14. The method of claim 1, wherein the second predetermined temperature is no more than 380° C.

15. The method of claim 1, wherein the first reaction zone, the second reaction zone, or both, has a temperature of not more than 420° C., whereby the final conversion product is a base stock for the production of high-octane gasoline.

16. The method of claim 1, wherein a catalyst bed temperature in one or more of the reaction zones does not exceed 420° C., whereby the final conversion product is a base stock for the production of high-octane gasoline.

17. The method of claim 1, wherein the first reaction zone, the second reaction zone, or both, has a temperature of not more than 500° C., whereby the final conversion product is a concentrate of alkylaromatics.

18. The method of claim 1, wherein a catalyst bed temperature in a reaction zone does not exceed 500° C., whereby the final conversion product is a concentrate of alkylaromatics.

19. The method of claim 1, wherein a demulsifier is added to the reaction water stream.

20. The method of claim 1, wherein the raw hydrocarbon fraction comprise a straight run hydrocarbon fraction of 65-85° C.

21. The method of claim 1, wherein the temperature of the first reaction zone is about 365 to 380° C.

22. The method of claim 1, wherein the second feed stream comprises one or more of methanol, water, ethylene, propylene, and other oxygenates.

23. A method of producing gasoline, the method comprising:
  a. supplying a first feed stream, comprising a raw hydrocarbon component;
  b. heating the first feed stream to a predetermined temperature;
  c. supplying the first feed stream at the first predetermined temperature to a reactor comprising a first reaction zone having a first temperature, the first reaction zone in fluid communication with a second reaction zone having a second temperature, the second reaction zone in fluid communication with an end reaction zone having a third temperature;
  each reaction zone comprising a zeolite catalyst;
  d. wherein the temperature of the end reaction zone is 40-70° C. lower than the temperature of the first zone reaction, the temperature of the second reaction zone or both; and,
  e. supplying a second feed stream, the second feed stream comprising one or more of methanol, other oxygenates, and olefins, heating and separating the second feed stream, whereby the second feed stream is split into a first flow and a second flow, wherein the first flow has a predetermined temperature and is supplied into the first reaction zone; and the second flow has a predetermined temperature and is supplied into the second reaction zone.

24. The method of claim 23, wherein the second feed stream consists essentially of an oxygenate and the olefin.

25. The method of claim 23, wherein the temperatures of the first reaction zone, the second reaction zone, or both are regulated without using heat exchange equipment.

26. The method of claim 23, wherein the temperature of the first reaction zone is controlled by feed rates and temperatures of the first feed stream and first flow; whereby the temperature of the first reaction zone is controlled without the using heat-exchangers.

27. The method of claim 23, comprising supply the first feed stream to a separation steps, wherein heavy hydrocarbon fractions are removed from the first feed stream prior to supplying the first feed stream to the reactor, whereby hydrocarbon components of the first feed stream entering the reactor have a molecular mass of no more than 180 and a boiling point of no more than 250° C., thereby reducing coking of the catalyst.

28. The method of claim 23, wherein the first reaction zone, the second reaction zone, or both, are adiabatic reactors.

29. The method of claim 23, wherein the first predetermined temperature is no more than 500° C.

30. The method of claim 23, wherein the first flow predetermined temperature is no more than 380° C.

31. The method of claim 23, wherein the first reaction zone, the second reaction zone, or both, has a temperature of not more than 420° C., whereby a conversion product is provided, wherein the conversion product is a base stock for the production of high-octane gasoline.

32. The method of claim 23, wherein the first reaction zone, the second reaction zone, or both, has a temperature of not more than 500° C., whereby a conversion product is provided, wherein the conversion product is a concentrate of alkylaromatics.

33. The method of claim 23, wherein the temperature of the first reaction zone is about 365 to 380° C.

34. A method of producing gasoline from raw hydrocarbon fractions, fractions of gaseous olefins and oxygenates, the method comprising:
- a. supplying a feedstock component having a temperature to a reactor, conducting a reaction on the feedstock component, wherein the reaction is carried out in the presence of a zeolite-containing catalyst, to thereby provide a conversion product; wherein the feedstock component comprises one or more of raw hydrocarbon fractions and fractions of gaseous olefins;
- b. wherein a high-octane gasoline is isolated by separation of the conversion product, while diverting simultaneously a reaction water and an exhaust gas; and,
- c. wherein the reactor comprises at least two reaction zones with a zeolite-containing catalyst;
- d. supplying a first supply stream comprising one or more of methanol, other oxygenates and olefins to a first reaction zone, and a second supply stream comprising one or more of methanol, oxygenates and olefins to a second reaction zone;
- e. wherein between the first and second reaction zones there is a mixer, whereby a reaction product from the previous reaction zone with the second supply stream is mixed; and,
- f. whereby the conversion product is provided from the reactor.

35. The method of claim 34, wherein a flow rate of the first, the second or both supply streams and the temperature of the feedstock component supplied to the reactor is controlled; whereby the maximum catalyst bed temperature in the first, the second or both reaction zones does not exceed: (i) 420° C. in the production of a base stock for the production of gasolines or (ii) 500° C. in the production of alkylaromatics concentrate.

36. The method of claim 34, wherein a rate of supply of the first supply stream is inversely related to the temperature of the feedstock component supplied to the reactor.

37. The method of claim 34, wherein the first supply stream is directed into a space upstream from the first reaction zone where the first supply stream is mixed with the feedstock component.

38. The methods of claim 34, 35 or 36, wherein the feedstock component is heated in two stages: wherein in a first stage, a raw hydrocarbon fraction or a mixture of the raw hydrocarbon fraction and the first supply stream are vaporized, heavier non-evaporated components are separated; and wherein in a second stage the vaporized components are superheated.

39. The method of claim 34, wherein the mixer comprises a bed of neutral material granules, a fraction of crushed quartz or both.

40. The method of claim 34, wherein the feedstock component and the first supply stream are fed through a mixer.

41. The method of claim 40, wherein the mixer comprises a bed of neutral material granules, a fraction of crushed quartz or both.

42. The method of claim 34, wherein the first and the second supply streams are supplied in a gaseous phase at a temperature of no more than 380° C., thereby preventing its decomposition upon heating.

43. The method of claim 34, wherein the reaction water is separated from the conversion product; the reaction water is supplied to a distillation column, thereby providing a distillation residue of which is water cleaned from residues of hydrocarbons with a reduced content of methanol and a distillate of which is water with an increased content of oxygenates and hydrocarbons, while methanol water and hydrocarbons produced during the distillation process are recycled to a reactor inlet to the beginning of the process in a mixture with methanol and/or other oxygenate and olefin-containing feedstock.

44. The methods of claim 1 or 34, wherein the catalyst comprises a synthetic amorphous aluminosilicate or an inorganic oxide used as a binder component, which is a mixture of alumina in an amount of 30-70 wt. % and silica in an amount of 70-30 wt. %.

45. The methods of claim 1 or 34, wherein the catalyst is based on crystalline pentasil-type aluminosilicate having a molar ratio of $SiO_2/Al_2O_3=25-100$ characterized by the presence of residual amounts of sodium ions being equivalent to a content of 0.05-0.1 wt. % of sodium oxide, containing said crystalline aluminosilicate and binder, wherein it further contains cobalt oxide, oxides of rare earth elements and zinc oxide in the following ratio, wt. %:
Zinc oxide: 0.5-3.0
Oxides of rare earth elements: 0.1-5.0
Cobalt oxide: 0.05-2.5
Crystalline aluminosilicate: 63-69.8
Binder: the rest.

46. The methods of claim 1 or 34, wherein the catalyst is based on the pentasil group zeolites, which contains a mechanical mixture of two zeolites having a different silicate module:
- a. first zeolite having a $SiO_2/Al_2O_3=20$ previously treated with an aqueous solution of alkali modified with oxides of rare earth elements (REE) in an amount of 0.5-2.0 wt. %, and
- b. second zeolite having $SiO_2/Al_2O_3=82$ having a residual amount of sodium oxide of 0.04 wt. % taken in the ratio of 1.7/1 to 2.8/1, and the remainder being a binder in an amount of 20 to 30 wt. % of the catalyst weight.

47. The methods of claim 1 or 34, wherein the catalyst is based on the pentasil group zeolites, which contains a mechanical mixture of two zeolites having a different silicate module:
- c. first zeolite previously treated with an aqueous solution of alkali modified with oxides of rare earth elements (REE) in an amount of 0.5-2.0 wt. %, and
- d. second zeolite having a residual amount of sodium oxide of 0.04 wt. % taken in the ratio of 1.7/1 to 2.8/1, and the remainder being a binder in an amount of 20 to 30 wt. % of the catalyst weight.

48. A plant for the production of gasolines from raw hydrocarbon fractions, fractions of gaseous olefins and oxygenates comprising:
- (a) a first unit, a second unit, a third unit and a reactor; wherein the units and the reactor are configured and associated such that:
  - (i) the first unit supplies a stream comprising one or more of methanol, other oxygenates, and olefins to the reactor;
  - (ii) the second unit supplies raw hydrocarbon fractions to the reactor;
  - (iii) the third unit supplies a flow to the reactor;
- (b) wherein the reactor comprises: a first reaction zone having a zeolite-containing catalyst; a second reaction zone; and, an outlet for subsequent separation of a conversion product;

(c) wherein the first and second units are adapted to supply the stream and the raw hydrocarbon fractions to the first reaction zone, and the stream to the second reaction zone; and (d) wherein between the reaction zones, there is located a mixer, whereby a reaction product from an upstream reaction zone and the stream is mixed.

49. The plant of claim 48, wherein, the first unit comprises: a first heater configured to heat the stream and which has at least two outputs, the first of which is connected to a first input of the first reaction zone directly or through the mixing zone, and the second of which is connected to a second input of the second reaction zone directly or through the mixing zone; the plant further configured for the supply of concentrated recovery water to the heating unit.

50. The plant of claim 49, wherein the first heater further comprises an evaporator configured to evaporate hydrocarbons; and a second heater configured to heat an evaporate from the evaporator; wherein between the heater and the evaporator there is a separator for removal of heavy hydrocarbon fractions containing mainly hydrocarbon components with a molecular mass of no more than 180 and with boiling point temperatures of up to 250° C. under normal conditions.

51. The plant of claim 48, further comprises a fourth unit, wherein the fourth unit is configured to determine a parameter of a produced gasoline and is connected to a control unit for the first unit thereby controlling the flow rate of the stream.

52. The plant of claim 48, wherein the reaction zones are arranged in series, in a vertical direction, or a horizontal direction.

* * * * *